US010844354B2

(12) United States Patent
Braam et al.

(10) Patent No.: US 10,844,354 B2
(45) Date of Patent: Nov. 24, 2020

(54) CARDIOMYOCYTE MATURATION

(71) Applicant: Ncardia B.V., Leiden (NL)

(72) Inventors: Stefan Robbert Braam, Leiden (NL);
Leon Tertoolen, Leiden (NL);
Christine Mummery, Leiden (NL)

(73) Assignee: NCARDIA B.V., Leiden (NL)

( * ) Notice: Subject to any disclaimer, the term of this patent is extended or adjusted under 35 U.S.C. 154(b) by 421 days.

(21) Appl. No.: 15/316,341

(22) PCT Filed: Jun. 5, 2015

(86) PCT No.: PCT/NL2015/050411
§ 371 (c)(1),
(2) Date: Dec. 5, 2016

(87) PCT Pub. No.: WO2015/187023
PCT Pub. Date: Dec. 10, 2015

(65) Prior Publication Data
US 2017/0159018 A1 Jun. 8, 2017

(30) Foreign Application Priority Data

Jun. 6, 2014 (NL) .................................. 2012961

(51) Int. Cl.
C12N 5/077 (2010.01)
(52) U.S. Cl.
CPC ........ C12N 5/0657 (2013.01); C12N 2500/25 (2013.01); C12N 2500/32 (2013.01); C12N 2500/34 (2013.01); C12N 2500/35 (2013.01); C12N 2500/36 (2013.01); C12N 2500/38 (2013.01); C12N 2500/90 (2013.01); C12N 2500/99 (2013.01); C12N 2501/01 (2013.01); C12N 2501/125 (2013.01); C12N 2501/155 (2013.01); C12N 2501/16 (2013.01); C12N 2501/165 (2013.01); C12N 2501/30 (2013.01); C12N 2501/395 (2013.01); C12N 2501/415 (2013.01); C12N 2501/727 (2013.01); C12N 2501/999 (2013.01); C12N 2506/02 (2013.01); C12N 2506/45 (2013.01); C12N 2533/90 (2013.01)

(58) Field of Classification Search
CPC .............. C12N 5/0657; C12N 2500/25; C12N 2500/32; C12N 2500/35; C12N 2500/36; C12N 2500/38; C12N 2500/99; C12N 2501/01; C12N 2501/125; C12N 2501/155; C12N 2501/16; C12N 2501/165; C12N 2501/395; C12N 2501/415; C12N 2501/727; C12N 2501/999; C12N 2506/02; C12N 2506/45; C12N 2533/90; C12N 2500/34; C12N 2500/90; C12N 2501/30
See application file for complete search history.

(56) References Cited

U.S. PATENT DOCUMENTS 6,562,619 B1 * 5/2003 Gearhart et al. ............... 435/366
2007/0204351 A1 * 8/2007 Davidson et al. ................ 800/3

FOREIGN PATENT DOCUMENTS

WO 2013/019661 A1 2/2013
WO 2014/200339 A1 12/2014

OTHER PUBLICATIONS

Rajala K. et al., "Cardiac Differentiation of Pluripotent Stem Cells", Stem Cells International, vol. 2011, Article ID 383709, total 12 pages. (Year: 2011).*
Grais I.M. et al., "Thyroid and the Heart", Am J Med., published online on Mar. 2014; print form as 2014, vol. 127, No. 8, pp. 691-698; attached author's manuscript, total pp. 1-16. (Year: 2014).*
Walz M.A. et al., "Thyroid effects on adenosine 3',5'-monophosphate levels and adenylate cyclase in cultured neuroblastoma cells" , Endocrinology, 1987, vol. 120, No. 4, pp. 1265-1271. (attached Abstract only). (Year: 1987).*
Lundy S.D. et al., "Structural and Functional Maturation of Cardiomyocytes Derived from Human Pluripotent Stem Cells", Stem Cells and Development, 2013, vol. 22, No. 14, pp. 1991-2002. (Year: 2013).*
Zhang, Donghui et al., "Tissue-engineered cardiac patch for advanced functional maturation of human ESC-derived cardiomyocytes", Biomaterials, Elsevier Science Publishers BV, Barking, GB, vol. 34, No. 23, May 23, 2013, pp. 5813-5820.
De Boer, Teun P. et al., "Beta-, Not Alpha-Adrenergic Stimulation Enhances Conduction Velocity in Cultures of Neonatal Cardiomyocytes", Circulation Journal, vol. 71, No. 6, Jun. 1, 2007, pp. 973-981.
Sartiani, Laura et al., "Developmental Changes in Cardiomyocytes Differentiated from Human Embryonic Stem Cells: A Molecular and Electrophysiological Approach", Stem Cells, Alphamed Press, Dayton, OH, US, vol. 25, No. 5, Jan. 1, 2007, pp. 1136-1144.
Pillekamp, Frank et al., "Contractile Properties of Early Human Embryonic Stem Cell-Derived Cardiomyocytes: Beta-Adrenergic Stimulation Induces Positive Chronotropy and Lusitropy but Not Inotropy", Stem Cells and Development, vol. 21, No. 12, Aug. 10, 2012, pp. 2111-2121.
Lee, Yee-Ki et al., "Triidothyronine Promotes Cardiac Differentiation and Maturation of Embryonic Stem Cells via the Classical Genomic Pathway", Molecular Endocrinology, Endocrine Society, Baltimore, MD, US, vol. 24, No. 9, Sep. 1, 2010, pp. 1728-1736.

(Continued)

Primary Examiner — Satyendra K Singh
(74) Attorney, Agent, or Firm — Browdy and Neimark, PLLC

(57) ABSTRACT

This disclosure generally concerns the fields of cell biology and molecular biology. In particular the invention concerns the field of stem cell biology and maturation of stem cell-derived cardiomyocytes. Disclosed is a method for improving the maturity of stem-cell derived cardiomyocytes, in particular of the ventricular type, as can be witnessed by, for example, an improved upstroke velocity of the stem-cell derived cardiomyocytes.

14 Claims, 6 Drawing Sheets

(56) References Cited

OTHER PUBLICATIONS

Figure 1:
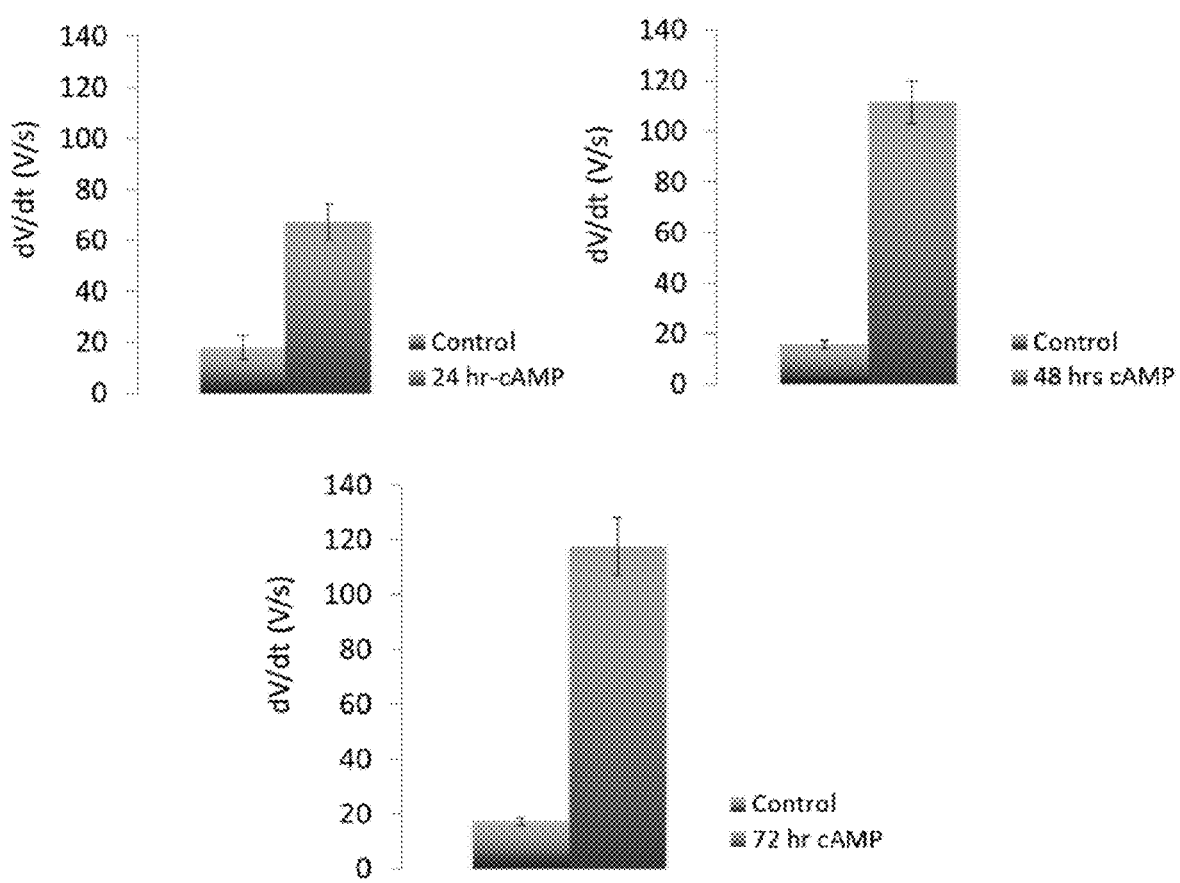

Andersson, Henrik et al., "Monitoring of troponin release from cardiomyocytes during exposure to toxic substances using surface plasmon resonance biosensing", Analytical and Bioanalytical Chemistry, Springer, Berlin, DE, vol. 398, No. 3, Aug. 9, 2010, p. 1395-1402.
Mauhin, Viviane, "International Search Report in PCT/NL2015/050411", dated Aug. 27, 2015, 5 pages, European Patent Office, Rijswijk, NL.
Mauhin, Viviane, "Written Opinion of the International Searching Authority PCT/NL2015/050411", dated Aug. 27, 2015, 8 pages, European Patent Office, Munich, DE.

\* cited by examiner

CARDIOMYOCYTE MATURATION

CROSS-REFERENCE TO RELATED APPLICATIONS

This application is a U.S. National Stage filing under 35 U.S.C. § 371 of International Application No. PCT/NL2015/050411, filed Jun. 5, 2015, which in turn claims priority to Dutch Patent Application No. 2012961, filed Jun. 6, 2014, the entire contents of which are incorporated by reference herein.

FIELD OF THE INVENTION

This disclosure generally concerns the fields of cell biology and molecular biology. In particular the invention concerns the field of stem cell biology and maturation of stem cell-derived cardiomyocytes. Disclosed is a method for improving the maturity of stem-cell derived cardiomyocytes, in particular of the ventricular type, as can be witnessed by, for example, an improved upstroke velocity of the stem-cell derived cardiomyocytes.

PRIOR ART

Human stem cells are human cells, that may be stably multiplied and cultured in vitro, that are, for example, pluripotent and may be totipotent. By that it is meant that the cells can differentiate into many different mature differentiated cell types of the human body and may, in fact, be able to differentiate into all of the cell types of an adult human body.

One example is human embryonic stem cells (hESCs), which are created from embryonic tissues and serially cultivated thereafter in an in vitro culture.

Another example are induced pluripotent stem cells (hiPSCs), which refers to a type of pluripotent stem cell artificially prepared from a non-pluripotent cell, typically an adult somatic cell, or a terminally differentiated cell, such as fibroblast, a hematopoletic cell, a neuron, an epidermal cell, or the like. These induced pluripotent stem cells are obtained by contacting the cell with reprogramming factors Both of these types of human pluripotent stem cells (hPSCs) can undergo differentiation in vitro to generate derivatives of the 3 primary germ layers and hence potentially all the cell types present in the body, including the differentiation into cardiomyocytes.

The successful isolation of human embryonic stem cells, and more recently, the generation of human induced pluripotent stem cells, has created new opportunities for cardiovascular therapies and research, for example in disease modelling and compound screening. In addition there is much interest in predicting cardiotoxicity of small compounds and receptor ligands by the use of stem-cell derived cardiomyocytes.

From having been difficult to control, human cardiomyogenesis in vitro is now becoming a process which, to a certain extent, can be effectively manipulated and directed. Successful directed cardiomyocyte differentiation from human pluripotent stem cells (hPSCs) has been reported over the last few year (see Burridge et al. Cell Stem Cell. 2012; 10:16-28). The stem cell-derived cardiomyocytes derived so far beat spontaneously, express the expected proteins and ion channels, show cardiac-type action potentials and calcium transients and show functional properties that are comparable to cardiomyocytes in the developing heart. Recently is was concluded that despite these promising results, many lines of evidence indicate that under the conditions currently used these stem-cell derived cardiomyocytes do not exhibit the morphological and functional characteristics of adult cardiomyocytes. Instead, the stem-cell derived cardiomyocytes described to date generally resemble immature embryonic/fetal cardiomyocytes, and they are in some functional and structural aspects different from adult cardiomyocytes (Vidarsson et al. Stem Cell Rev. 2010; 6(1):108-20). This appears true for cardiomyocytes derived from hESCs and for cardiomyocytes derived from hiPSCs (see, for example, Yang et al. Circ Res. 2014; 114:511-523).

It is however beneficial to have cardiomyocytes, in particular populations of cardiomyocytes with cells having a more pronounced metabolic maturity, or at least, that show reduced fetal, immature or hypertrophic characteristics. Therefore reproducible and efficient protocols that improve the state of maturity of human pluripotent stem cells, already differentiated into cardiomyocytes, are highly desirable in the field.

DESCRIPTION

Definitions

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

It is contemplated that any method or composition described herein can be implemented with respect to any other method or composition described herein. Embodiments discussed in the context of methods and/or compositions of the invention may be employed with respect to any other method or composition described herein. Thus, an embodiment pertaining to one method or composition may be applied to other methods and compositions of the invention as well.

All the methods of the invention may be used on mammals and mammalian cells. In a preferred embodiment, all the methods of the invention may be used on humans or human cells.

As used herein "a" or "an" may mean one or more. When used in conjunction with the word "comprising", the words "a" or "an" may mean one or more than one.

"Cardiomyocytes" refers to any cardiomyocyte lineage cells; the cells may be at any stage of cardiomyocyte ontogeny, unless otherwise specified. The skilled person distinguishes two types of cells in the heart: cardiomyocyte cells and cardiac pace maker cells. Cardiomyocytes include atrial type cardiomyocytes, ventricular type cardiomyocytes, and/or conducting system cardiomyocytes (see e.g. Maltsev et al, Mech Dev. 1993 November; 44(1):41-50) or Cardiac Regeneration using Stem Cells (10 Apr. 2013); Keiichi Fukuda, Shinsuke Yuasa CRC Press. ISBN 9781466578401. The current invention relates to cardiomyocytes, including, but not limited to those mentioned above.

For example, cardiomyocytes may include both cardiomyocyte precursor cells and mature cardiomyocytes. The term "stem cell-derived cardiomyocytes" as used herein refers to cardiomyocytes that are generated from pluripotent stem cells, for examples from human pluripotent stem cells such as human embryonic stem cells or human induced pluripotent stem cells, by the process of differentiation. In particular, within the context of the current invention, the term "stem cell-derived cardiomyocytes" refers to such cardiomyocytes obtained by in vitro culturing, for example by in vitro differentiation of (human) pluripotent stem cells. Such stem cell-derived cardiomyocytes can be defined as spontaneously contractile cells derived by in vitro methods from a human pluripotent cell, although sometimes non-contractile cells can be obtained. Such cells still manifest other of the typical characteristics of cells that were in vitro differentiated into cardiomyocytes, and using differentiation protocols aimed at obtaining stem-cell derived cardiomyocytes and are in the art also referred to as (in vitro obtained) stem-cell derived cardiomyocytes. Recent reviews defining and described stem-cell derived cardiomyocytes, within the context of the current invention, have covered methods to create (e.g. Vidarsson et al. Stem Cell Rev. 2010; 6(1):108-120, Boheler et al. Circ Res. 2002; 91(3):189-201. Mummery et al. Circ Res. 2012; 111(3):344-358, and Jiang et al. J Cell Mol Med. 2012; 16(8):1663-1668, David et al. Physiology (Bethesda) 2012; 27(3):119-129), and purify (Habib et al. J Mol Cell Cardiol. 2008; 45(4):462-474) such stem-cell derived cardiomyocytes, as well as their electrophysiology (Blazeski et al. Prog Biophys Mol Biol. 2012; 110(2):178-195), and these methods and media, for example based on APEL (StemCell Technologies) and StemPro34 (Invitrogen), used are well known to the skilled person.

For example, Mummery et al describes the several approaches for differentiation of human pluripotent stem cells to stem-cell derived cardiomyocytes, in particular by applying embryoid body, monolayer culture, or inductive co-culture. Methods for forming embryoid bodies range from a simple enzymatic partial dissociation of pluripotent stem cell colonies to various methods to more precisely control embryoid body cell number and size using microwells with forced aggregation (centrifugation), microwells to first expand pluripotent stem cells colonies to a defined size, and micropatterned pluripotent colonies of defined sizes. Alternatively, propagating pluripotent stem cells as monolayers on Matrigel with defined media can be used for cardiogenesis. For both embryoid bodies and monolayer approaches, stage-specific application of key growth factors (e.g. BMP4, ActivinA, FGF2, Wnt agonists and antagonists, and VEGF) in defined media are important for optimal cardiogenesis, although some protocols use fetal bovine serum or small molecules to induce cardiogenesis. Co-culture of mechanically passaged pluripotent stem cells with visceral endodermal-like END2 cells takes advantage of cell signaling from END2 cells to promote cardiogenesis. Other sources of method for differentiating stem-cells into cardiomyocytes include Kehat et al. Clin. Invest. 2001; 108, 407-414, Mummery et al., Circulation. 2003; 107, 2733-2740, and Laflamme et al. 2007; Nat. Biotechnol. 25, 1015-1024.//PCT Cardiomyocytes directly obtained from an adult or mature heart, e.g. human heart, are understood to not be "stem cell-derived cardiomyocytes" within the context of the current disclosure.

"Maturity" of the stem-cell derived cardiomyocytes relates to the developmental process of maturation, and that is required for a cell, i.e. a cardiomyocyte, to attain its fully functional state. Differentiated cells derived from stem cells, for example embryonic stem cells or induced pluripotent stem cells often exhibit a "fetal" state of development. Such differentiated stem-cell derived cardiomyocytes are often in an embryonic, fetal or immature state of development. Maturation of such embryonic, fetal or immature stem-cell derived cardiomyocytes thus may lead to loss of at least one functional characteristic associated with an embryonic, fetal or immature state of the cells and gain of functional characteristics associated with adult or mature cells. For example, maturation of the stem-cell derived cardiomyocytes may require the loss of fetal gene and/or protein expression and associated functional characteristics, and the acquisition of gene expression and functional characteristics that are associated with adult or mature cells. In other words, stem-cell derived cardiomyocyte that matures, or of which the maturity is improved, shows at least one functional characteristic that, in comparison to a stem-cell derived cardiomyocyte that has not or to a lesser extent matured, more resembles the functional characteristics as generally observed in adult or mature cardiomyocytes. In particular, within the context of the current invention, maturity of the stem-cell derived cardiomyocytes relates to the functional characteristic related to the electrophysiological characteristics of the cardiomyocyte, for example the resting membrane potential, the upstroke velocity, conduction, action potential, and others (see for example Blazeski et al. Prog Biophys Mol Biol. 2012; 110(0): 166-177.) Other typical features of maturation of stem-cell derived cardiomyocytes include the development or improvement of contractile force, the expression of particular cardiomyocyte specific markers and a shift to fatty acid metabolism.

"Stem cells" are cells that may be stably multiplied and cultured in vitro and that are totipotent, pluripotent, induced pluripotent, multipotent, oligopotent, or unipotent cells, preferably at least pluripotent. By that it is meant that the cells can differentiate into (many) different mature differentiated cell types of the (human or animal) body and may, in fact, be able to differentiate into all of the cell types of an adult (human or animal) body.

"Embryonic stem cells" are pluripotent stem cells derived from early embryos. Embryonic stem cells are pluripotent cells derived from the inner cell mass of a blastocyst. Methods for obtaining, maintaining and culturing embryonic cells for use in the method disclosed herein are well-known to the skilled person, for example, as described by Chung et al. (Cell Stem Cell. 2008; (2):113-117). This method describes human embryonic stem cell generated without embryo destruction. The term includes embryonic stem cells obtained from cultures of ES cell lines.

"Induced pluripotent stem cells", or iPSCs, refer to a type of pluripotent stem cell that is artificially prepared from a non-pluripotent cell, for example from an adult somatic cell, or terminally differentiated cell, such as fibroblast, a hematopoietic cell, a myocyte, a neuron, an epidermal cell, or the like. The iPSCs are obtained by treating the non-pluripotent cell with reprogramming factors, by various method known to the skilled person, for example as described by Takahashi et al. (Cell. 2007; 131(5):861-72). Such iPSCs can differentiate into cell types of the three germ layers in vitro and in teratomas. Induced pluripotent stem (iPS) cells are cells that have the characteristics of embryonic stem cells.

The term "pluripotent stem cell" refers to a cell capable of being differentiated into cells of all three germinal layers (endoderm, mesoderm and ectoderm). Although in theory a pluripotent stem cell can differentiate into any cell of the body, the experimental determination of pluripotency is generally based on differentiation of a pluripotent cell into several cell types of each germinal layer. The pluripotent stem cell may for example be an embryonic stem or an induced pluripotent stem cell derived by reprogramming somatic cells.

A "medium" as used herein refers to an aqueous solution, including buffers, suitable for maintaining human or animal cells for a sufficient period. For example, a medium is suitable if it allows the treatment of cells for a period required to obtain the effect intended by the treatment. The term "medium" also includes growth medium that are suitable for the in vitro cell culture of human or animal cells. A "defined medium" as used herein refers to a (growth) medium suitable for the in vitro cell culture of human or animal cells and in which all of the chemical components are known. Such defined medium does not or essentially not comprise any ill-defined source of nutrients and/or other ill-defined factors. Within the context of the current invention the defined medium (or medium) used may still contain defined amounts of products such as (purified) albumin, growth factors, and hormones, but is essential free of serum (i.e. less than 1% w/w, preferably less than 0.5% w/w. even more preferably less than 0.1% w/w, even more preferably less than 0.05% w/w of the medium ready for use, most preferably the medium is free of serum (i.e. 0% w/w serum; albeit it might contain defined amount of specified compounds like (recombinant) albumin. Although widely used, serum has many limitations. It contains high levels of numerous and unknown proteins and compounds which interfere dramatically with the small quantities of the desired proteins produced by the cells. The presence of serum may also affect in vitro testing results with the cells obtained since some compounds may bind up to 99% to serum proteins . . . . Another limitation is the serum batch-to-batch inconsistencies, resulting in serious regulatory concern about various serum protein contaminations in the product.

As used herein "epigenetic memory" refers to inheritance systems also referred to cell memory, i.e. to heritable changes in gene activity or expression that are not caused by changes in the DNA sequence (see Jablonka et al., J. Theor. Biol. 1992 158 (2): 245-268). Such epigenetic changes are preserved when cells divide, for example in induced pluripotent stem cells that are the consequence of reprogramming see, for example, Kim et al. Nature Biotechnology 2011; 29, 1117-1119 and Liang et al., Cell Stem Cell 2013; 13, 149-159.).

Conventional techniques as used herein refers to a situation wherein the methods of carrying out the conventional techniques used in methods of the invention will be evident to the skilled worker. The practice of conventional techniques in molecular biology, biochemistry, cell culture, genomics, sequencing and related fields are well-known to those of skill in the art and are discussed, for example, in the following literature references: Human Embryonic Stem Cell: The Practical Handbook. Publisher: John Wiley & Sons, LTD, Editors (Sullivan, S., Cowan, C. A., Eggan, K.) Harvard University, Cambridge, Mass., USA (2007); Human Stem Cell, a Laboratory Guide (2nd Edition) by Peterson, S., and Loring, J. F. (2012).

DETAILED DESCRIPTION

While performing experiments aimed at improving the maturity, in particular the electrophysiological maturity, of stem-cell derived cardiomyocytes (in particular cardiomyocytes obtained by in vitro culturing of (pluripotent) stem cells like (human) embryonic stem cells and/or (human) induced pluripotent stem cells), it was surprisingly found that exposing cell that already differentiated from stem cell into cardiomyocytes, albeit that are preferably still at an embryonic, fetal or immature state of development, to a condition that increases cAMP under the culturing conditions used, leads to improved maturation, in particular electrophysiological maturation, of the stem-cell derived cardiomyocytes. This is in comparison to stem-cell derived cardiomyocytes that were continued to be cultured under identical culturing conditions, except for the cAMP increasing condition, and/or in comparison to stem-cell derives cardiomyocytes that were not continued to be cultured under the cAMP increasing condition.

Thus, in a first aspect of the disclosure there is provided for a method of improving maturity of stem-cell derived cardiomyocytes, wherein the method comprises the step of cultivating the cells under a condition of increased cAMP, preferably by exposing the stem-cell derived cardiomyocytes to a cAMP-raising compound in a medium. In other words, the cells are held or cultured under a condition wherein cAMP, preferably intracellular cAMP is increased or elevated. Thus the cells are cultured in a medium in the presence of elevated cAMP; or under the condition of elevated cAMP. Elevation of the cAMP (or increasing the cAMP) is relative to cells that are cultivated in a medium under conditions wherein cAMP is not or less elevated. The presence of elevated cAMP (or increased cAMP) during the cultivation may be accomplished by any suitable mean, preferably by exposing the cells to a cAMP-raising compound, well-known to the skilled person. By cultivating the cell under culture conditions that promote cAMP pathway activity, for example by cultivating the cells under culture conditions promoting elevated cAMP, preferably by exposing the cells to a cAMP-raising compound, maturity of the stem-cells, as defined herein, is improved. In other words cells with more mature characteristics, typical for cardiomyocytes are obtained in comparison to cells not cultures under such conditions of elevated cAMP. Preferably the medium is a defined medium that is essentially serum-free.

In the method, stem-cell derived cardiomyocytes are cultivated under a condition of increased cAMP, for example exposed to a cAMP-raising compound, i.e. a compound that leads to increased levels of cyclic AMP in the culture and under the conditions used. Such conditions can be appropriately defined. For example, the stem-cell derived cardiomyocytes may be exposed to the cAMP-raising compound at a temperature that is suitable for the stem-cell derived cardiomyocytes, for example at a temperature of about 31° C., 32° C., 33° C., 34° C., 35° C., 36° C., 37° C., 38° C., or 39° C., and/or at a $CO_2$-concentration in the air between 1-10%, preferably 2-6%, and/or with an oxygen tension between 1-20%, for example, 1%, 5%, 10%, 15% or 20%.

The cAMP-raising compound may be added to or already be present in the medium. Depending on how long the stem-cell derived cardiomyocytes will be exposed to the cAMP-raising compound, the exposure may include replacement of the defined medium with new medium, preferably a defined medium that is essentially serum-free. That medium may not, but preferably, may again comprise a cAMP-raising compound. Alternatively, additional cAMP-raising compound may be added to the medium, preferably a defined medium that is essentially serum-free, in time, for example in case the cAMP-raising compound present in the medium is inactivated or consumed during the exposure to the stem-cell derived cardiomyocytes.

The stem-cell derived cardiomyocytes are exposed to at least one cAMP-raising compound, but combinations of different cAMP-raising compounds are also contemplated. Such combination of different cAMP-raising compounds may be present in the same medium, preferably a defined medium that is essentially serum-free, or may be used in sequence (i.e. in case medium is replaced during the maturation). For example, cells may first be exposed to a first cAMP-raising compound present in a first medium, followed by, for example addition of a second cAMP-raising compound at a later moment during the exposure, or followed by, for example the replacement of the medium with the first cAMP-raising compound by a medium comprising a second cAMP-raising compound.

The stem-cell derived cardiomyocytes are cultured in the medium, preferably a defined medium that is essentially serum-free (chemically defined medium). The medium, preferably a defined medium that is essentially serum-free, may be any suitable medium for maintaining the stem-cell derived stem cells, and is preferably a defined medium that is suitable for maturation of the stem-cell derived cardiomyocytes. Suitable defined media are known to the skilled person and include those for example described in Mummery et al. Circ Res. 2012; 111(3):344-358, and as already discussed above, and such media as disclosed herein.

In a preferred embodiment, the cAMP levels are elevated, for example the administration of the cAMP raising compound raises the (intracellular) levels of cAMP at least 5%, at least 10%, preferably at least 20%, at least 30%, at least 50%, at least 100%, or even at least 150% above normal. The skilled person can, without undue burden establish suitable conditions of elevated cAMP within the context of the current invention, for example by using a cAMP raising compound in increasing amount, in order to provide for the condition of elevated cAMP of for example at least 5%, at least 10%, preferably at least 20%, at least 30%, at least 50%, at least 100%, or even at least 150% relative to the normal, control, situation.

As discussed above, the skilled person is well aware of various methods to provide for the stem-cell derived cardiomyocytes to be exposed to the cAMP raising compound in the medium (i.e. to be cultivated in the presence of elevated cAMP), preferably defined medium that is essentially serum-free.

Although not necessary, it was found when the stem-cell derived cardiomyocytes were exposed in the medium to not only elevated cAMP, for example by a cAMP-increasing compound, but also to a thyroid hormone or a thyroid hormone analog, preferably triiodothyronine or 3,5-diiodothyropropionic acid (DIPTA or DITPA), maturation, for example as witnessed from the electrophysiological characteristics of the thus obtained stem-cell derived cardiomyocytes can be even further improved. Other thyroid hormone analogs include GC-1 compounds (which is a thyroid hormone receptor subtype beta (TRbeta) selective agonist from Bristol-Myers Squibb), RO compounds (which is a thyroid hormone receptor subtype beta 1 (TRbeta) selective agonist from Roche Pharmaceuticals), CO23 compound (which is a thyroid hormone subtype alpha 1 (TRalpha1) selective agonist from KaroBio), KB2115 (which is a thyroid hormone receptor subtype beta (THbeta) selective agonist from KaroBio). In other words, by exposing the stem-cell derived cardiomyocytes to combination of a cAMP increasing or raising compound and a thyroid hormone or a thyroid hormone analog, maturation of these cells, e.g. from an embryonic, fetal or immature state of development to a more adult state of development is improved.

Thyroid hormones (THs) are phylogenetically ancient and primary form of TH is 3,3',5,5'tetra-iodo-l-thyronine (thyroxine or T4). T4 is converted to the more active form of TH, 3,3',5 tri-iodo-l-thyronine (T3; 2S)-2-amino-3-[4-(4-hydroxy-3-iodo-phenoxy)-3,5-diiodo-phenyl]propanoic acid). The T4 to T3 conversion occurs through the activity of deiodinases whose expression is regulated by cortisol. Both T3 and T4 can be used within the context of the current invention.

Therefore, according to a preferred embodiment, the medium, preferably defined medium that is essentially serum-free, further comprises a thyroid hormone or a thyroid hormone analog, preferably triiodothyronine or 3,5-diiodothyropropionic acid (DITPA). As will be understood by the skilled person other thyroid hormones and/or thyroid hormone analogs may be used in as far as these mimic the function of triiodothyronine or 3,5-diiodothyropropionic acid, for example within the context of the current disclosure. The thyroid of thyroid hormone analog, preferably triiodothyronine, may be present in the medium at a final concentration of 0.0001 to 500 ng/ml of the medium to be used, preferably 0.001 to 400 ng/ml, more preferably 0.01-300 ng/ml, even more preferably 0.1-200 ng/ml, for example between 1-150 ng/ml, and/or 20-140 ng/ml, and/or 40-110 ng/ml. DITPA may for example by used in a final concentration of 0.01 nM to 10 μM of DITPA, preferably about 0.1 nM to 8 μM of DITPA, preferably about 0.2 nM to 6 μM of DITPA, preferably 0.3 nM to 5 μM of DITPA, preferably about 0.4 nM to 4 μM of DITPA, preferably about 0.5 nM to 3 μM of DITPA, preferably about 0.6 nM to 2 μM of DITPA, more preferably about 0.75 nM to 1.5 μM of DITPA. Although preferably the thyroid hormone and/or thyroid analog are present in the medium together with the cAMP raising compound, it is also contemplated that the stem-cell derived cardiomyocytes are treated sequentially with the cAMP-raising compound and the thyroid hormone and/or thyroid hormone analog, for example by replacement of the medium. Alternatively, exposure of the stem-cell derived cardiomyocytes may be initiated with the cAMP-raising compound followed by later addition to the medium of the thyroid hormone or thyroid hormone analog.

Although in principal a stem-cell derived cardiomyocytes at any stage of development may be used, preferably the stem-cell derived cardiomyocytes that will be exposed to the elevated cAMP, for example to the at least one cAMP-raising compound, show an embryonic, fetal or immature state of development, i.e. the share characteristics with embryonic or fetal cardiomyocytes (in vivo, i.e. in a developing embryo or fetus). The skilled person is well aware of the different stages of maturation phases of (human) stem cell-derived cardiomyocytes (see for a concise review Robertson et al. (StemCells 2013; 31:829-837). It is to note that also the stem cells from which the cardiomyocytes are derived may also have been cultivated under the condition of elevated cAMP, for example during differentiation into the cardiomyocytes.

Stem-cell derived cardiomyocytes showing such embryonic, fetal or immature state of development, i.e. such early phase stem-cell derived cardiomyocytes can, for example, be defined as contractile cells, with some proliferative capacity and with embryonic like electrophysiology (i.e., small negative membrane potential and small action potential amplitude). Late phase cells, or mature stem-cell derived cardiomyocytes can be defined by loss of proliferative capacity and a more adult human cardiomyocyte-like electrophysiology. Different elements of maturity appear to be affected by line, time in culture, co-cultured cells, and culture conditions. Adult cardiomyocytes may be large and cylindrical 'brick-like' (approximately 150*10 micrometer for ventricular cells), while embryonic and fetal cardiomyocytes are smaller with a reduced sarcomeric organization. Similarly, early phase stem-cell derived cardiomyocytes are small and round to slightly oblong (e.g. approximately 5-10 micrometer diameter), whereas late phase stem-cell derived cardiomyocytes develop a more oblong morphology. In general early phase stem-cell derived cardiomyocytes proliferate at a lower rate than their pluripotent progenitors whereas late phase stem-cell derived cardiomyocytes hPSC-CM can be considered non-proliferating cells. The transcriptional profile of stem-cell derived cardiomyocytes is different from their originating pluripotent stem cells and well-known differences include loss of pluripotency transcription factors and up regulation of cardiac markers).

The metabolic maturity can be determined by methods known to the skilled person, for examples methods that look at phenotype, morphology, gene expression, metabolic markers, cell surface markers, electrophysiological characteristics and/or cellular functional assay of the cell. For example, for maturation one can determine decreased expression of genes associated with a "fetal" state or cardiac hypertrophic state such as, for example, NPPA (ANF) and NPPB (BNP), or preferably, determine the electrophysiological characteristics of the maturing stem-cell derived cardiomyocytes, and wherein a more adult cardiomyocyte characteristic can be seen for more maturated stem-cell derived cardiomyocytes, as discussed in detail herein.

In addition the relative maturity of stem-cell derived cardiomyocytes can be determined by the presence of decreased expression of genes associated with the a fetal state, such as NPPA, NPPB, smooth muscle actin and skeletal actin, or the increasing expression of adult genes/proteins, such as myosin light chain 2V, calsequestrin and ryanodine receptor).

Thus, preferably the stem-cell derived cardiomyocytes to be cultivated in the presence of elevated cAMP, e.g. to be exposed to (at least) the cAMP-raising compound show an embryonic, fetal or immature state of development.

The length of incubation of the stem cell-derived cardiomyocytes with the cAMP raising compound may be any length as long as it is sufficient to provide for a more mature stem-cell derived cardiomyocyte in comparison to such stem cell-derived cardiomyocytes either treated for the same period under identical conditions, but without the cAMP-raising compound, or in comparison to the stem cell-derived cardiomyocytes not treated for that period. So, for example, the exposure to the cAMP-raising compound may, for example, be for between four, ten and twenty days, although good results were obtained with (much) shorter periods of exposure. Therefore, preferably, the stem-cell derived cardiomyocytes are exposed to (at least) the cAMP-raising compound (ie. to the presence of elevated cAMP) for a period selected from the group consisting of at least 2 hours, at least 6 hours, at least 8 hours, at least 12 hours, at least 16 hours, at least 24 hours, at least 30 hours, at least 48 hours, at least 60 hours and at least 72 hours, and preferably no more than 30 days. As mentioned, the cAMP may be elevated/increased at any time during the cultivation in the method of the invention. Preferably, the cells, preferably human cells, are exposed to the condition of elevated CAMP, i.e. exposed to the cAMP raising compound, after the cells have been differentiated, for example, 5, 6, 7, 8, 9, 10 days after the cell differentiated into cardiomyocytes (that would normally be about 15-30 days after the stem cells were first cultivated under conditions of differentiation of the cells into cardiomyocytes).

As detailed above, the skilled person is well aware of characteristics of adult cardiomyocytes, and is therefore well aware of methods to determine improved maturation of the stem-cell derived cardiomyocytes within the context of the current disclosure. In particular it was found that the electrophysiological characteristics of the stem-cell derived cardiomyocytes exposed to the cAMP-raising conditions or compound showed more adult-like characteristics. In particular is was found that the stem-cell derived cardiomyocytes exposed to the cAMP-raising compounds, i.e. cultivated under elevated cAMP conditions, showed an more adult-like (i.e. improved maturation) upstroke velocity (dV/dtmax), determined by standard techniques in the art, in particular with the method as described by for example, Bellin et al. (EMBO J. 2013; 32(24): 3161-3175), with the modification that in the examples provide herein spontaneous activity of the stem-cell derived cardiomyocytes was determined and no electric stimulation was required, although measurement may, as the skilled person knows, also be done under conditions of stimulation.

Thus, in one embodiment maturity of the stem-cell derived cardiomyocyte is determined by at least determining the upstroke velocity of the stem-cell derived cardiomyocytes cultivated in the presence of increased cAMP, preferably exposed to the cAMP-raising compound, and wherein the upstroke velocity of the stem-cell derived cardiomyocytes cultivated in the medium in the presence of elevated cAMP, preferably exposed to the cAMP-raising compound is found to be higher than the upstroke velocity of stem-cell derived cardiomyocytes not cultivated in the medium in the presence of elevated cAMP, preferably exposed to the cAMP-raising compound. Thus, in other words, by the cultivated in the medium in the presence of elevated cAMP, preferably exposure of the stem-cell derived cardiomyocytes to (at least) the cAMP-raising compound, the upstroke velocity of the thus treated stem-cell derived cardiomyocytes is more adult cardiomyocyte like (i.e. improved maturation) in compared to non-treated stem-cell derived cardiomyocytes, and that will display a more fetal or embryonic cardiomyocyte like upstroke velocity.

For example, adult cardiomyocytes (ventricular cardiomyocytes) have been reported to have an upstroke velocity (dv/dtMax) of about 215-235 V/s whereas stem-cell derived cardiomyocytes, in particular spontaneously beating cardiomyocytes, only show an upstroke velocity of 10-40 V/s (see, for example, Hoekstra et al. Frontiers in Physiology, Cardiac Electrophysiology 2012; 3: article 346). In contrast, the stem-cell derived cardiomyocytes, in particular human stem-cell derived cardiomyocytes, treated with the method according to this disclosure can be found to show an upstroke velocity of at least 50 V/s, at least 60 V/s, at least 80 V/s, at least 100 V/s, at least 140 V/s, or even at least 180 V/s, as can be witnessed from the examples, whereas the non-treated stem-cell derived cardiomyocytes showed an upstroke velocity of about 20 V/s (in line with the values reported in the prior art). In particular high upstroke velocity (e.g. between at least 160 V/s-180 V/s) may be obtained by exposing the stem-cell derived cardiomyocytes to both the compound that increases cAMP during the exposure, and the thyroid hormone or thyroid hormone analog. Therefore, there is also provided for a method of increasing the upstroke velocity of stem-cell derived cardiomyocytes, the method comprising treating the stem-cell derived cardiomyocytes with a cAMP-raising compound, and as disclosed herein. In particular, there is provided for a method for increasing the upstroke velocity of the stem-cell derived cardiomyocytes with a factor of at least 1.5, at least 2, at least 3, at least 4, at least 5 fold compared to non-treated cells.

As mentioned it was found that, independent of the upstroke velocity, the electrophysiological characteristics of the stem-cell derived cardiomyocytes cultivated in the medium in the presence of elevated cAMP, e.g. exposed to the cAMP-raising compound showed more adult stem-like characteristics. In particular is was found that the stem-cell derived cardiomyocytes cultivated in the medium in the presence of elevated cAMP, i.e. exposed to the cAMP-raising compounds showed an more adult-like (i.e. improved maturation) resting membrane potential, determined by standard techniques in the art, in particular with the method as described by for example, Bellin et al. (EMBO J. 2013; 32(24): 3161-3175), with the modification that in the examples provide herein spontaneous activity of the stem-cell derived cardiomyocytes was determined and no electric stimulation was required as the cells obtained were spontaneously beating/active. Non-spontaneous beating stem-cell derived cardiomyocytes may require stimulation in the determination of the electrophysiological characteristics.

Thus, in one embodiment maturity of the stem-cell derived cardiomyocyte is determined by at least determining the resting membrane potential of the stem-cell derived cardiomyocytes cultivated in the medium in the presence of elevated cAMP, i.e. exposed to the cAMP-raising compound, and wherein the resting membrane potential of the stem-cell derived cardiomyocytes cultivated in the medium in the presence of elevated cAMP, i.e. exposed to the cAMP-raising compound is found to be lower (i.e. a more negative value) than the resting membrane potential of stem-cell derived cardiomyocytes not cultivated in the medium in the presence of elevated cAMP, or exposed to the cAMP-raising compound. Thus, in other words, by the exposure of the stem-cell derived cardiomyocytes to increased cAMP by (at least) the cAMP-raising compound, the resting membrane potential of the thus treated stem-cell derived cardiomyocytes is more adult cardiomyocyte like (i.e. improved maturation) in compared to non-treated stem-cell derived cardiomyocytes, and that will display a more fetal or embryonic cardiomyocyte like upstroke velocity.

For example, adult cardiomyocytes (ventricular cardiomyocytes) have been reported to have a resting membrane potential of about −82 to −87 mV, whereas stem-cell derived cardiomyocytes, in particular spontaneously beating cardiomyocytes, only show a resting membrane potential (sometime referred to as maximum diastolic potential of about −63 to −64 mV (see, for example, Hoekstra et al. Frontiers in Physiology, Cardiac Electrophysiology 2012; 3: article 346). In contrast, the stem-cell derived cardiomyocytes, in particular human stem-cell derived cardiomyocytes, treated with the method according to this disclosure can be found to show a resting membrane potential of −66 mV or less, more preferably −70 mV or less, even more preferably −75 mV or less, even more preferably −78 mV or less, most preferably −80 mV or less (for example −81 mV or −82 mV), as can be witnessed from the examples, whereas the non-treated stem-cell derived cardiomyocytes showed a resting membrane potential of about −64 mV (in line with the values reported in the prior art). Therefore, there is also provided for a method of lowering the resting membrane potential of stem-cell derived cardiomyocytes, the method comprising treating the stem-cell derived cardiomyocytes with (at least) a cAMP-raising compound, and as disclosed herein. In particular, there is provided for a method for lowering the resting membrane potential of the stem-cell derived cardiomyocytes with at least 3 mV, 6 mV, 8 mV, 10 mV, 12 mV or at least even 15 mV, in general no more than 20 mV or 15 mV, as compared to non-treated cells.

In a preferred embodiment in the method disclosed herein both the upstroke velocity and the resting membrane potential may be improved, relative to non-treated cells, e.g. to the values described above. Thus, preferred, the upstroke velocity of the stem-cell derived cardiomyocytes cultivated in the medium in the presence of elevated cAMP, or exposed to the cAMP-raising compound is at least 50 V/s, at least 60 V/s, at least 80 V/s, at least 100 V/s, at least 140 V/s, or at least 180 V/s and the resting membrane potential of the stem-cell derived cardiomyocytes cultivated in the medium in the presence of elevated cAMP, i.e. exposed to the cAMP-raising compound is −66 mV or less, more preferably −70 mV or less, even more preferably −75 mV or less, even more preferably −78 mV or less, most preferably −80 mV or less, for example −81 mV or −82 mV.

According to the current disclosure any kind of cAMP raising compound may be used in the method the invention, for example to improve the maturity of the stem-cell derived cardiomyocytes. However, preferably the cAMP-raising compound is selected from the group consisting of a cAMP-degrading enzyme inhibitor, a cAMP-phosphodiesterase inhibitor, a cAMP-raising drug, a cAMP-raising hormone, an adenylyl cyclase activator, a cAMP analog, IBMX, GLP-1, GIP, glucagon, forskolin, dibutyryl-cAMP and isoproterenol.

Additional examples of compounds that may be used include an effective amount of thyrocalcitonin, calcitonin, glucagon-like peptide-1, Exendin-3 and Exendin-4. Other cAMP raising (or elevating) agents may be adrenocorticotropic hormone, MECA, HE-NECA, adrenamedullin, a-Neo-Endorphin, b-MSH, a-MSH, and the like. cAMP analog, wherein said cAMP analog is selected from the group consisting of 9-pCPT-2-O-Me-cAMP, 8-Br-cAMP, Rp-cAMPS, 8-Cl-cAMP, Dibutyryl cAMP, pCPT-cAMP, and N6-monobutyryladenosine 3',5'-cyclic monophosphate, PDE inhibitors (e.g., cAMP-specific PDEs), adenylate cyclase activators, and activators of ADP-ribosylation of stimulatory G proteins are further examples of cAMP modulating agents described herein.

Analogs of cAMP include 8-pCPT-2-O-Me-cAMP (e.g., 8-(4-chlorophenylthio)-2'-O-methyladenosine 3',5'-cyclic monophosphate); 8-Br-cAMP (e.g., 8-bromoadenosine 3',5'-cyclic monophosphate); Rp-cAMPS (e.g., Rp-adenosine 3',5'-cyclic monophosphorothioate); 8-Cl-cAMP (e.g., 8-chloroadenosine 3',5'-cyclic-monophosphate); Dibutyryl cAMP (e.g., N6,2'-O-dibutyryladenosine 3',5'-cyclic monophosphate); pCPT-cAMP (e.g., 8-(4-chlorophenylthio)adenosine 3',5'-cyclic monophosphate); and N6-monobutyryladenosine 3',5'-cyclic monophosphate. Exemplary PDE inhibitors include: theophylline (e.g., 3,7-dihydro-1,3-dimethyl-1H-purine-2,6-dione; 2,6-dihydroxy-1,3-dimethylpurine; 1,3-dimethylxanthine), caffeine (e.g., 1,3,7-trimethylxanthine); quercetin dihydrate (e.g., 2-(3,4-dihydroxyphenyl)-3,5,7-trihydroxy-4H-1-benzopyran-4-one dihydrate; 3,3',4',5,7-pentahydroxyflavone dihydrate); rolipram (e.g., 4-[3-(cyclopentyloxy)-4-methoxyphenyl]-2-pyrrolidinone); 4-(3-butoxy-4-methoxybenzyl)imidazolidin-2-one; propentofylline (e.g., 3,7-dihydro-3-methyl-1-(5-oxobexyl)-7-propyl-1H-purine-2,6-dione; 3-methyl-1-(5-oxohexyl)-7-propylxanthine); 3-isobutyl-1-methylxanthine (e.g., 3,7-dihydro-1-methyl-3-(2-methylpropyl)-1H-purine-2,6-dione; IBMX; 3-isobutyl-1-methyl-2,6(1H,3h)-purinedione; 1-methyl-3-isobutylxanthine); 8-Methoxymethyl-3-isobutyl-1-methylxanthine (e.g., 8-methoxymethyl-IBMX); enoximone (e.g., 1,3-dihydro-4-methyl-5-[4-methylthiobenzoyl]-2H-imidazol-2-one); papaverine hydrochloride (e.g., 6,7-Dimethoxy 1-veratrylisoquinoline hydrochloride).

Exemplary activators of adenylate cyclase include: forskolin.

Other agents reported to increase intracellular cAMP include fenoldopam methanesulphonate, dopamine hydrochloride, apomorphine hydrochloride, histamine phosphate, ACTH, sumatriptan succinate, prostaglandin F2alpha tromethamine, prostaglandin E1, prostaglandin I2, iloprost tromethamine, prostaglandin E2, misoprostol, sulproston, ATP disodium salt, pindolol, secretin, cisapride, phentolamine methanesulphonate, nemonapride, clozapine, sertindole, olanzapine, risperidone, sulpiride, levosulpride, chlorpromazine, hydrochloride, haloperidol, domperidone, fluphenazine dihydrochloride/decanoate/enantate, fluphenazine dihydrochloride/decanoate, fluphenazine dihydrochloride, ATP (adenosin triphosphate), ATP (adenosin triphosphate) disodium salt, ketanserin, ketanserin tartare, metergoline, pindolol, prazosin hydrochloride, Yohimbine, yohimbine hydrochloride, theophylline, caffeine, theobromine, aminophylline, amrinone, milrinone, naltrexone, naloxone, albuterol, levalbuterol, metaproterenol, terbutaline, pirbuterol, salmeterol, bitolterol, colterol, dobutamine, 8L-arginine-vasopressin, 8-lysine-vasopressin, desmopressin, methyldopa, DOPA, rauwolshine, prazosin, phentolamine, quinidine, dapiprazole, loxiglumide, chorionic gonadotropin, follitropin-alpha, follitropin-beta (FSH), menotropin (LH, FSH), oxytocin, somatostatin antagonists, RMP-7, ACE inhibitors (like captopril), misoprostol, latanoprost, PGE1, alprostadil, somatropin (GH, PRL) secretagogues (MK-677), tabimorelin (NN-703, pamorelin, NNC-26-0323, TRH, cosyntropin, corticorelin, glucagon, enteroglucagon, PTH 1-34, cocaine, amphetamine, dextroamphetamine, metamphetamien, phenmetrazine, methylphenidate, diethylpropion, metyrosine, reserpine, minoxidil, sulfasalazine, levamisole, and thalidomide, fluoride, aminophylline, paraxanthine, pentoxifyllinetheobromine, theophylline, EHNA (erythro-9-(2-hydroxy-3-nonyl)adenine), BAY 60-7550 (2-[(3,4-dimethoxyphenyl)methyl]-7-[(1R)-1-hydroxyethyl)-4-phenylbutyl]-5-methyl-imidazo[5,1-f][1,2,4]triazin-4(1H)-one), Oxindole, PDP (9-(6-Phenyl-2-oxohex-3-yl)-2-(3,4-dimethoxybenzyl)-purin-6-one), Inamrinone, milrinone Enoximone Anagrelide, Cilostazol. Mesembrine, Rolipram, Ibudilast, Piclamilast, Luteolin, Drotaverine, Roflumilast, Sildenafil, tadalafil, vardenafil, udenafil avanafil Dipyridamole icariin, 4-Methylpiperazine Papaverine, It will be understood that, in the nature of the current disclosure the skilled person can establish the concentration and duration of exposure required for each individual compound or combination of compounds that can improve maturation of the stem-cell derived cardiomyocyte, as can, for example be established based on an improved upstroke velocity and/or resting membrane potential.

It is preferred the method is performed in vitro, in other words, the cells are cultured or exposed under in vitro conditions, i.e. outside a body, preferably outside a human body.

In accordance with the nature of the current disclosure, the method according to the invention, can advantageously be applied to any type of stem-cell derived cardiomyocyte, in particular in vitro obtained stem-cell derived cardiomyocytes. Therefore there is provided for a method as disclosed herein wherein the stem-cell derived cardiomyocytes are stem-cell derived cardiomyocytes obtained by in vitro culturing of stem-cells, preferably wherein the stem-cells are selected from the group consisting of totipotent stem cells, pluripotent stem cells, induced pluripotent stem cells multipotent stem cells, oligopotent stem cells, unipotent stem cells, even more preferably wherein the stem-cells are selected from the group consisting of embryonic stem cells, fetal stem cells, adult stem cells, most preferably wherein the stem-cells are selected from the group consisting of human embryonic stem cells, human fetal stem cells, human adult stem cells or human induced pluripotent stem cells.

Preferably the stem-cell derived cardiomyocytes are human stem-cell derived cardiomyocytes, for example human embryonic stem cell derived cardiomyocytes or human induced pluripotent stem cells derived cardiomyocytes.

As disclosed above, any kind of medium suitable for maintaining stem-cell derived cardiomyocytes as disclosed herein are suitable. However in particular it was found that the medium used to expose the stem cell derived cardiomyocyte to the (at least) elevated cAMP e.g. with the cAMP raising compound preferably is a defined medium further comprising at least one compound selected from the group consisting of L-carnitine (for example 0.5 mM-3.5 mM), creatine (for example 1.0-10.0 mM), taurine (for example, 0.5-20 mM), insulin (for example 1-15 ng/L), transferrin (for example 2-15 ng/L), selenium (for example 0.005 mg-0.01 mg/L), fatty-acids, preferably selected from linolenic acid (for example 0.001-20 microgram/ml), linoleic acid (for example 0.001-20 microgram/ml) and palmitic acid (for example, example 0.001-20 microgram/ml) cholesterol (for example 1-4 microgram per ml), polyvinylalcohol, preferably 0.1-10 mg/ml polyvinylalcohol, α-Monothioglycerol (for example, about 0.5-2 w/w %) and (bovine) serum albumin (for example 0.01-0.5 W/w %). Preferably all the above compounds are present (with or without thyroid hormone and/or thyroid hormone analog, as detailed above). For example a medium as described in the accompanying examples can advantageously be used.

The medium preferably may comprise glucose in concentrations of about 0-5000 mg/l glucose. Preferably the medium comprises 0-3000 mg/l glucose, more preferably 0-1500 mg/l, for example 1000 mg/l glucose (5.5 mM). The medium may also be free of glucose.

Also provided is a method of obtaining cardiomyocytes s with increased up stroke velocity and/or reduced resting membrane potential, wherein the cardiomyocytes are obtained from in vitro culturing of stem cells, the method comprising cultivating the cardiomyocytes in a medium in the presence of elevated cAMP. In contrast to cell not obtained with the methods disclosed herein, the cardiomyocytes obtained by the method according to the invention show basal values of resting membrane potential and/or upstroke velocity as disclosed herein, for example in claims 5-9, 16-19. The cells are distinguishable from cells in the prior art in that, when determining the resting membrane potential and/or upstroke velocity, the cells according to the invention do not need to be stimulated in order to obtain the values for these parameters as disclosed herein. In other words, the cells obtained with the method of the invention inherently, and without the need of further stimulation, for example with isoproterenol, prior or during measuring the resting membrane potential or upstroke velocity, have the property that is has with an upstroke velocity of at least 50 V/s, at least 60 V/s, at least 80 V/s, at least 100 V/s, at least 140 V/s, or at least 180 V/s, and/or have the property of a resting membrane potential of −66 mV or less, more preferably −70 mV or less, even more preferably −75 mV or less, even more preferably −78 mV or less, most preferably −80 mV or less, for example −81 mV or −82 mV. The cells according to the invention show this property without further stimulation of the cells, for example using isoproterenol, as is commonly done in the prior art.

Also provided is a stem-cell derived cardiomyocyte obtainable or obtained by the method according to the invention, for example a human (induced) pluripotent stem-cell derived cardiomyocyte, obtained by in vitro culturing, using the methods as disclosed herein.

Also provided is a, or a collection of, spontaneous beating in vitro obtained stem-cell derived cardiomyocyte(s) with an upstroke velocity of at least 50 V/s, at least 60 V/s, at least 80 V/s, at least 100 V/s, at least 140 V/s, or at least 180 V/s. Thus in this embodiment, when the cell of collection of cells are analyzed for upstroke velocity values of at least at least 50 V/s, at least 60 V/s, at least 80 V/s, at least 100 V/s, at least 140 V/s, or at least 180 V/s are measured. Thus provided is a, or a collection of, spontaneous beating in vitro obtained stem-cell derived cardiomyocyte(s) wherein the cardiomyocyte has the property that is has an upstroke velocity of at least 50 V/s, at least 60 V/s, at least 80 V/s, at least 100 V/s, at least 140 V/s, or at least 180 V/s. Thus in this embodiment, when the cell of collection of cells are analyzed for upstroke velocity values of at least at least 50 V/s, at least 60 V/s, at least 80 V/s, at least 100 V/s, at least 140 V/s, or at least 180 V/s are measured. As mentioned above, the cells have the property under basic conditions, without the need of further stimulation.

Also provided is a, or a collection of, induced pluripotent stem-cell derived cardiomyocyte, preferably a spontaneous beating induced pluripotent stem-cell derived cardiomyocyte with, or wherein the cardiomyocyte has the property that is has, an upstroke velocity of at least 50 V/s, at least 60 V/s, at least 80 V/s, at least 100 V/s, at least 140 V/s, or at least 180 V/s. The induced pluripotent stem-cell derived cardiomyocyte, preferably a spontaneous beating induced pluripotent stem-cell derived cardiomyocyte that can be obtained, for example, as disclosed herein are characterized in that, although the show adult-like cardiomyocyte properties, they, at the same time have the epigenetic memory of the cells that were used for the generation of the induced pluripotent stem cells, in particular human induced pluripotent stem cells (see, for example, Kim et al. Nature Biotechnology 2011; 29, 1117-1119 and Liang et al., Cell Stem Cell 2013; 13, 149-159 (2013).). The skilled person is well aware of methods to detect such epigenetic differences Thus in particular induced pluripotent stem-cell derived cardiomyocyte with an upstroke velocity of at least 50 V/s, at least 60 V/s, at least 80 V/s, at least 100 V/s, at least 140 V/s, or at least 180 V/s are provided and that have a epigenetic memory that is different from the epigenetic memory of adult cardiomyocytes. For example, induced pluripotent stem-cells derived from fibroblasts, umbilical cord blood cells, neonatal keratinocytes, late-outgrowth endothelial progenitor cells and renal tubular cells (e.g. as present in urine), but if fact induced-pluripotent stem-cells from any source will contain epigenetic information from its original source.

Also provided is a, or a collection of, spontaneous beating stem-cell derived cardiomyocyte according to the current disclosure, wherein the spontaneous beating stem-cell derived cardiomyocyte, or the collection, has the property that is has a resting membrane potential of −66 mV or less, more preferably −70 mV or less, even more preferably −75 mV or less, even more preferably −78 mV or less, most preferably −80 mV or less, for example −81 mV or −82 mV. Thus in this embodiment, when the cell of collection of cells are analyzed for resting membrane potential values of −66 mV or less, more preferably −70 mV or less, even more preferably −75 mV or less, even more preferably −78 mV or less, most preferably −80 mV or less, for example −81 mV or −82 mV are measured. Again the cells will show such values under conditions that do not need the further stimulation of the cells.

The preferred embodiments discussed above are equally applicable to these cells, and are included by reference for this use, and are not repeated for the sake of brevity only.

According to another aspect of the invention, there is provided for the use of a cAMP-raising compound, preferably a cAMP-raising compound and a thyroid hormone or thyroid hormone analog, for improving maturity of stem-cell derived cardiomyocytes, for increasing upstroke velocity of stem-cell derived cardiomyocytes, and/or for reducing the resting membrane potential of stem-cell derived cardiomyocytes.

Also provided for it the use of stem-cell derived cardiomyocytes obtainable by the method disclosed herein, or a cardiomyocyte a disclosed herein, and as obtainable by the method disclosed herein, in an method for identifying a modulator of cardiomyocytes, preferably wherein the method is to determine toxicity of a candidate modulator, to screen for candidate modulators, or to determine efficacy of a candidate modulator, or in cellular therapy. Such method are well-known to the skilled person.

The preferred embodiments discussed above are equally applicable to the above uses, are included by reference for these uses, and are not repeated for the sake of brevity only.

In a last aspect there is provided for a kit comprising stem-cell derived cardiomyocytes, a cAMP-raising compound and a medium, preferably defined medium that is essentially serum-free. It will be understood the cAMP-raising compound may already be present in the culture medium (or stock suitable for preparing the culture medium), but may also be separately present in the kit. The kit may further comprise a thyroid like hormone compound, as detailed above. Again, the preferred embodiments discussed above are equally applicable to the above kits, are included by reference for these kits, and are not repeated for the sake of brevity only.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

EXAMPLES

The present invention is further illustrated, but not limited, by the following Examples. From the above discussion and these Examples, one skilled in the art can ascertain the essential characteristics of the present invention, and without departing from the teaching and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1. Stem-Cell Derived Cardiomyocytes

Stem-cell derived cardiomyocytes to be treated with the method disclosed herein may be obtained by any method described in the art and known to the skilled person. For the current examples human pluripotent embryonic stem cells or human induced pluripotent stem cells were cultured in medium on mitotically inactivated mouse fibroblasts and passaged using TrypLE Select (Invitrogen). The medium contains DMEM/F12 (Gibco, cat. no. 11320-033), 20% (v/v) knockout serum replacement (Gibco, cat. no. 10828-028), 10 mM non-essential amino acids (Gibco, cat. no. 11140-050), 2 mM L-glutamine (Gibco, cat. no. 25030-081) 2b-mercaptoethanol (Gibco, cat. no. 21985-023), 10 ng/ml human bFGF.

One day before differentiation, cells were passaged onto matrigel coated 6-well plates at a density of 1 million cells/well in stem cell medium.

Cells were differentiated in embryoid bodies (EB). At day 0, cells were collected and re-suspended at 6×104 cells ml-1 in basic differentiation medium (serum-free) comprising a lipid mixture (2.2 microgram/ml cholesterol, 0.1 microgram/ml of linoleic acid, 0.1 microgram/ml of linolenic acid, and 0.1 microgram/ml of palmitic acid), insulin (1 mg/L), transferrin (0.55 mg/L), selenium (0.00067 mg/L), trace elements, 20 ng ml-1 of BMP4 (R&D Systems) and 30 ng ml-1 activin A (R&D Systems), 30 ng ml-1 VEGF (R&D systems), 40 ng ml-1 SCF (R&D systems) and 1.5 µM Chir99021 (Axon medchem). An amount of 50 µl of this mix was placed into each well of a 96-well round-bottom non-adherent plate yielding EBs composed of 3,000 cells. On day 3, 7, 10, 14 and 17, the medium was replaced with differentiation medium without growth factors.

The (fetal-like/immature) cardiomyocytes produced by this method are suitable for use in the method of the invention as taught herein, i.e. the maturation of said fetal-like (immature) cardiomyocytes may be improved using the methods disclosed herein.

Example 2. Differentiation in Monolayer

Alternatively human pluripotent embryonic stem cells or human induced pluripotent stem cells were cultured in monolayer according to the method described in Dambrot et al (2014), Exp. Cell. Res. dx.doi.org/10.1016/j.yexcr.2014.05.001; available online 13 May 2014. In short, the cells were cultured on Matrigel (BD Biosciences)-coated tissue culture dishes in mTeSR1 according to the manufacturer's protocol (Stem Cell Technologies). To initiate differentiation to cardiomyocytes, the cells were dissociated into small clusters of cells and seeded onto a Matrigel-coated cell culture dish in mTeSR1. Three days later (differentiation day (d) 0), the medium was replaced with low insulin (1 mg/l) (LI)-BPEL medium and supplemented with BMP4 (day 0-day 3), Activin A (day 0-day 3), CHIR99021 (day 0-day 3) and XAV939 (day 3-day 6). From day 6 onward BMP4, Activin A, CHIR99021 and XAV939 were absent from the medium.

The (fetal-like/immature) cardiomyocytes produced by this method are suitable for use in the method of the invention as taught herein, i.e. the maturation of said fetal-like (immature) cardiomyocytes may be improved using the methods disclosed herein.

Example 3. Generation of Matured Cardiomyocyte from Fetal-Like (Immature) Cardiomyocytes in In Vitro Culture Differentiated (fetal-like/immature) human stem-cell derived cardiomyocytes were subsequently cultured and allowed to mature as described below, although any other method in the art may suitable be used. Tissue culture plastic was coated using Matrigel (Corning) at a concentration of 1/100 in DMEM, for 45 min at room temperature. A single cell suspension coming from dissociated embryoid bodies, dissociated monolayers or (commercially obtained) frozen (fetal-like (immature)) stem-cell derived cardiomyocytes were seeded at an appropriate density on matrigel coated tissue culture plastic (e.g. in 20-40 k cells per well of a 96-well plate, e.g. 20-200 k per well of a 12 well plate). On day 1 following plating, the foetal-like (immature) cardiomyocytes were exposed to a culture medium composition of the invention, which consists of a serum-free culture medium composition comprising 50 ng/ml of T3 (Sigma T6397), 2 mM of carnitine, 5 mM of creatine, 5 mM of taurine, 2.2 microgram/ml of cholesterol, 0.1 microgram/ml of linoleic acid, 0.1 microgram/ml of linolenic acid, 0.1 microgram/ml of palmitic acid (lipids, for example, from Gibco 11905), 10 mg/ml of insulin, 5.5 mg/ml of transferrin, 0.0067 mg/ml of selenium (insulin, transferrin and selenium from e.g. Gibco 51500), 0.01% of trace element mix B (as described herein; Cellgro 99-175-CL), 0.1% of trace element mix C (as described herein; Cellgro 99-176-CL), 0.5 w/w % of antibiotics (penicillin-streptomycin mixture commercially available Gibco (Gibco 12070; 5000 U/ML), 0.05 mg/ml ascorbic acid, 2 mM of Glutamax supplement (i.e. L-alanyl-L-glutamine dipeptide in 0.85% NaCl, commercially available at Gibco, e.g. Gibco 35050), 0.125 w/w % polyvinylalcohol (PVA), 450 nM of alpha monothiolglycerol (MTG) (commercially available), 025 w/w %/o BSA (Bovostar BSAS1.0) in 46.5% (w/w) IMDM (Gibco 21056) and 46.5% (w/w) HAM F-12 with glutamax (Gibco 31765). All concentrations are expressed as final concentration in the culture medium composition. This step was repeated every 2-3 days. In those experiments that also use thyroid hormone or a thyroid hormone analog, treatment with the culture medium composition as taught herein comprising e.g. T3 started either at day 1, day 3 or day 7 post plating.

At day 10 dbcAMP was added to a final concentration of 0.5 mM and the cell were further cultured. Action potential measurements of control and dbcAMP treated cells were performed using the patch clamp technique at 24, 48 and 72-hours post addition of the cAMP-raising compound.

Example 4. Electrophysiology

Electrophysiology of the cells treated with the cAMP-raising compound or not was determined by standard techniques in the art, in particular with the method as described by for example, Bellin et al. (EMBO J. 2013; 32(24): 3161-3175), with the modification that in the examples provide herein spontaneous activity of the stem-cell derived cardiomyocytes was determined and no electric stimulation was required, although measurement may, as the skilled person knows, also be done under conditions of stimulation. Action potentials from small groups of cells (5-10 cells) were measured with the perforated patch clamp technique using an Axopatch 200b amplifier (Molecular Devices) and low resistance patch pipettes (1.5-2.5 MΩ). Data acquisition and analyses of action potentials were performed with pClamp 10 (axon instruments) and custom made software. Action Potentials were corrected for the calculated liquid junction potential (−15 mV).

Action potential from spontaneous beating cells were measured at 37±0.20 C using a modified Tyrode's solution containing (in mM): 140 NaCl, 5.4 KCl, 1.8 CaCl2, 1.0 MgCl2, 5.5 glucose, 5.0 HEPES; pH7.2 (NaOH).

The pipette solution contained (in mM): 125 K-gluconate, 20 KCl, 5 NaCl, 0.22 amphotericin-B, 10 HEPES; pH 7.2 (KOH). The resting membrane potential (RMP), maximal upstroke velocity (Vmax), AP amplitude (APA), and AP duration (APD) at 20, 50 and 90% repolarization (APD50, and APD90, respectively) were analyzed. Data from 10 consecutive action potentials were averaged.

Example 5 Results

The results can be witnessed from the various FIGS. 1-6, showing that treatment with a cAMP-raising compound as disclosed herein improves various electrophysiological characteristics of the stem-cell derived cardiomyocytes, including upstroke velocity, resting membrane potential, action potential, amplitude and repolarization.

FIG. 1 shows a comparison between the upstroke velocity of induced pluripotent stem cells that were treated with or without a cAMP-raising compound dbcAMP for various periods (24 hrs. 48 hrs. and 72 hrs.). Whereas the non-treated cells showed relative low upstroke velocities, treatment with the cAMP-raising compound improved the upstroke velocity dramatically (i.e. the values are more adult cardiomyocyte like). Comparable data may be obtained with human embryonic stem-cell derived cardiomyocytes, other human induced pluripotent stem-cell derived cardiomyocytes and/or with other cAMP-raising compounds.

Figure 2:
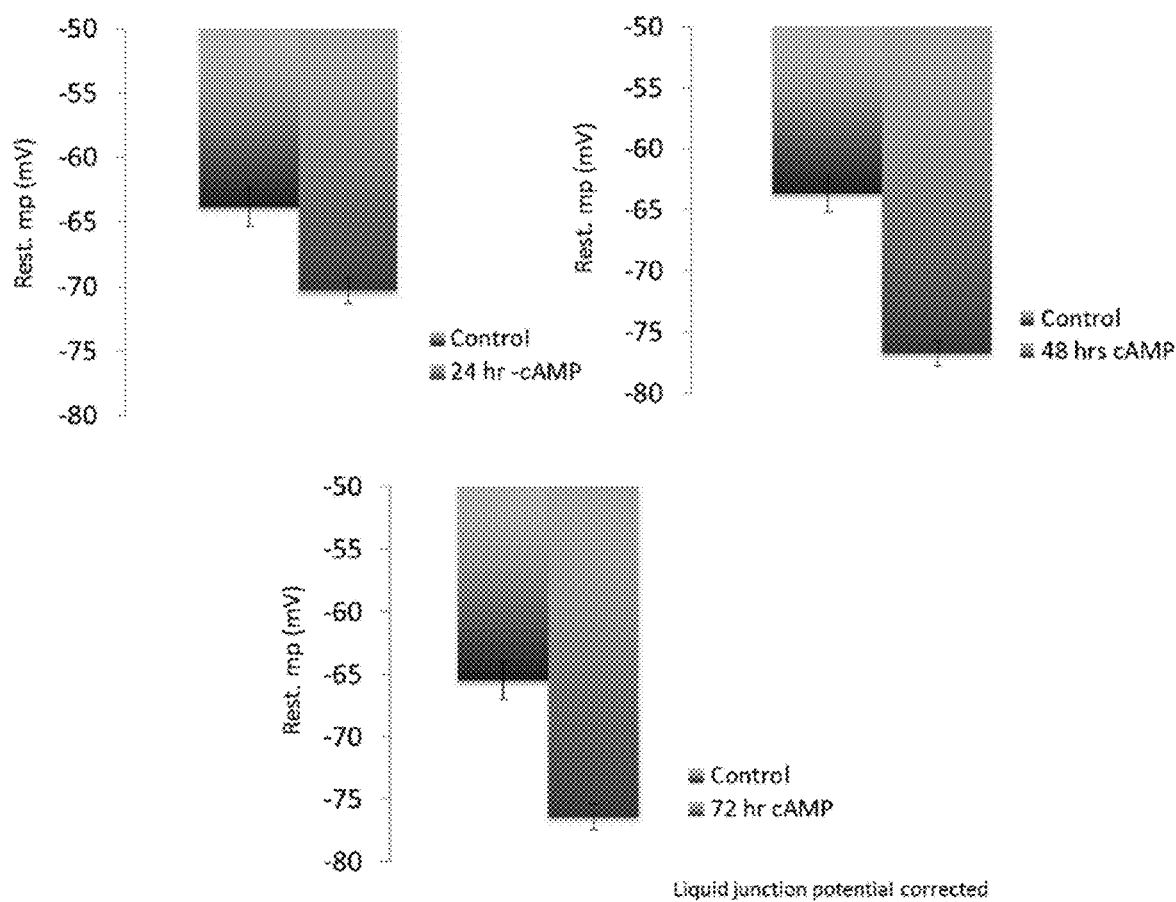

FIG. 2 shows a comparison between the resting membrane potential (liquid junction potential corrected) of induced pluripotent stem cells that were treated with or without a cAMP-raising compound dbcAMP for various periods (24 hrs., 48 hrs. and 72 hrs.). Whereas the non-treated cells showed relative fetal cardiomyocyte like values (e.g. around −63 mV), treatment with the cAMP-raising compound improved the resting membrane potential dramatically (i.e. the values are more adult cardiomyocyte like). Comparable data may be obtained with human embryonic stem-cell derived cardiomyocytes, other human induced pluripotent stem-cell derived cardiomyocytes and/or with other cAMP-raising compounds.

Figure 3:
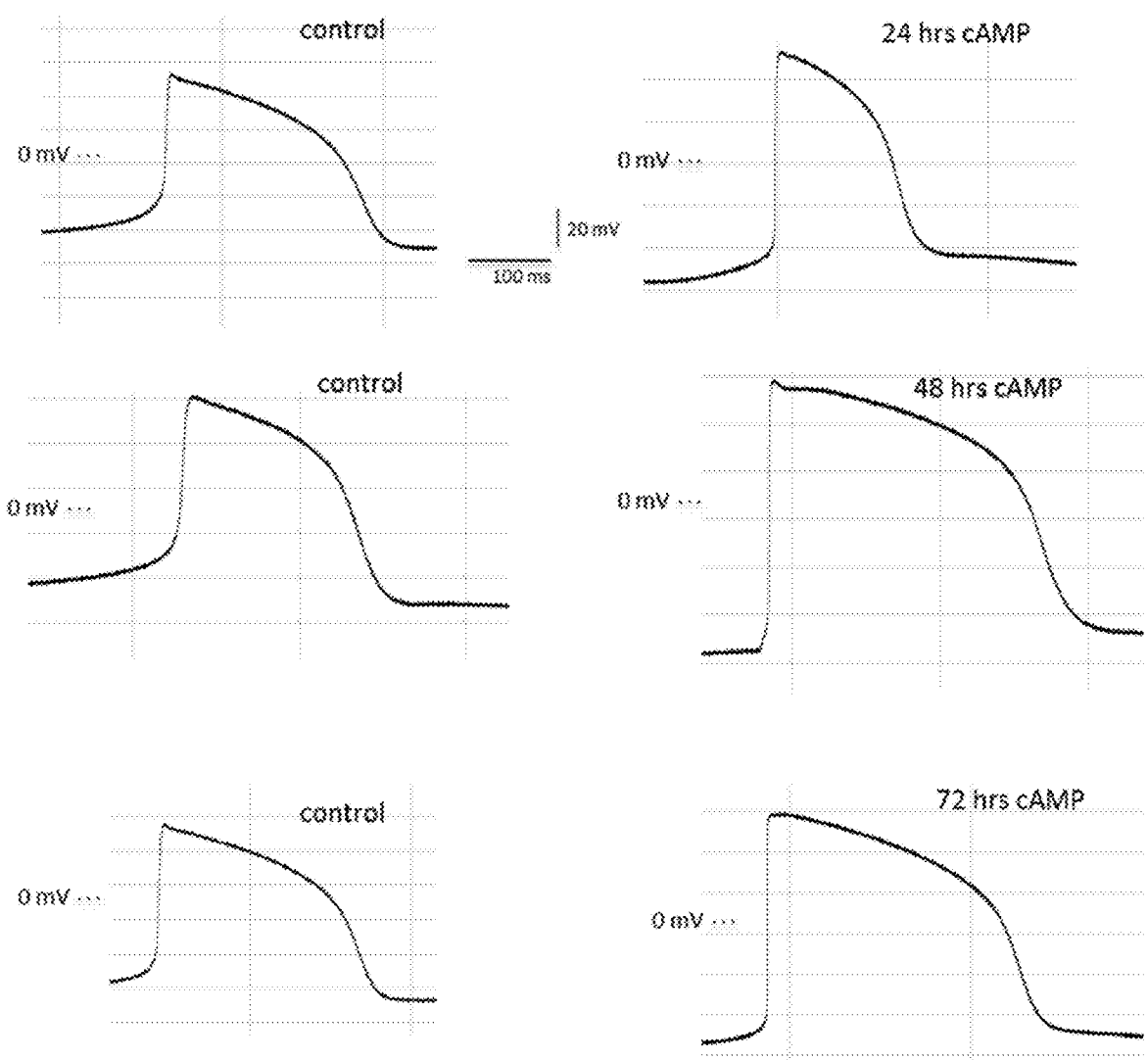

FIG. 3 shows a comparison between representative action potentials of induced pluripotent stem cells that were treated with or without a cAMP-raising compound dbcAMP for various periods (24 hrs., 48 hrs. and 72 hrs.). Whereas the non-treated cells showed relative fetal cardiomyocyte like values, treatment with the cAMP-raising compound leads to action potentials that are more adult cardiomyocyte like. Comparable data may be obtained with human embryonic stem-cell derived cardiomyocytes, other human induced pluripotent stem-cell derived cardiomyocytes and/or with other cAMP-raising compounds.

Figure 4:
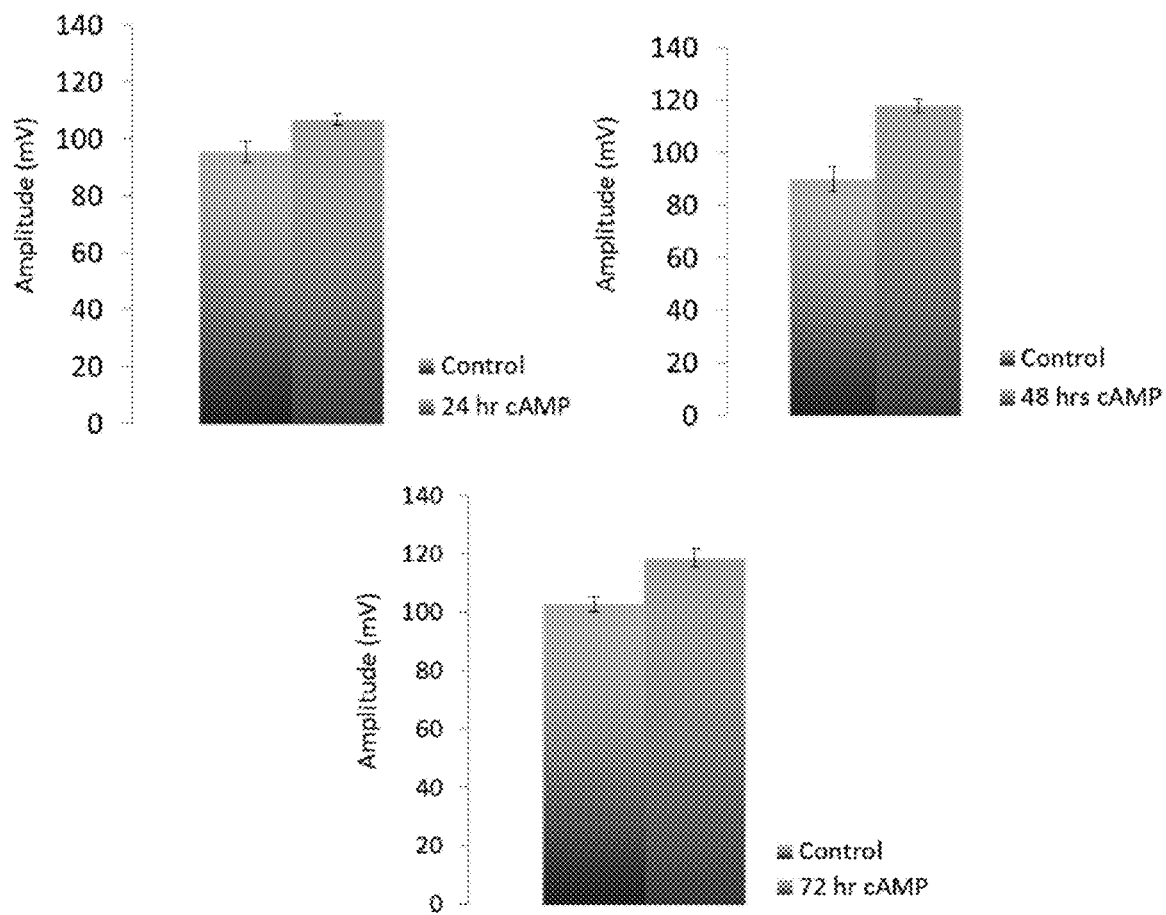

FIG. 4 shows a comparison between the amplitude of induced pluripotent stem cells that were treated with or without a cAMP-raising compound dbcAMP for various periods (24 hrs., 48 hrs. and 72 hrs.). A cAMP-raising compound improves the amplitude. Comparable data may be obtained with human embryonic stem-cell derived cardiomyocytes, other human induced pluripotent stem-cell derived cardiomyocytes and/or with other cAMP-raising compounds.

Figure 5:
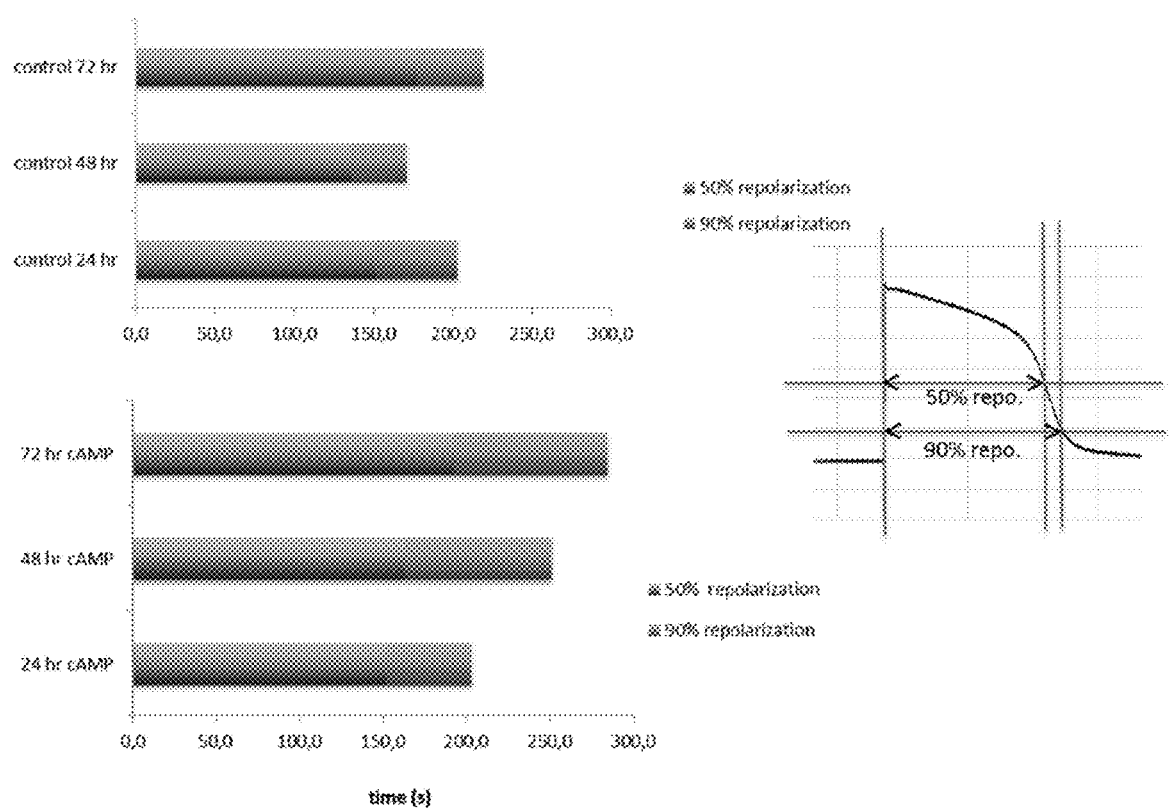

FIG. 5 shows the repolarization parameters of induced pluripotent stem cells that were treated with or without a cAMP-raising compound dbcAMP for various periods (24 hrs., 48 hrs. and 72 hrs.). A cAMP-raising compound improves the repolarization parameters. Comparable data may be obtained with human embryonic stem-cell derived cardiomyocytes, other human induced pluripotent stem-cell derived cardiomyocytes and/or with other cAMP-raising compounds.

Figure 6:
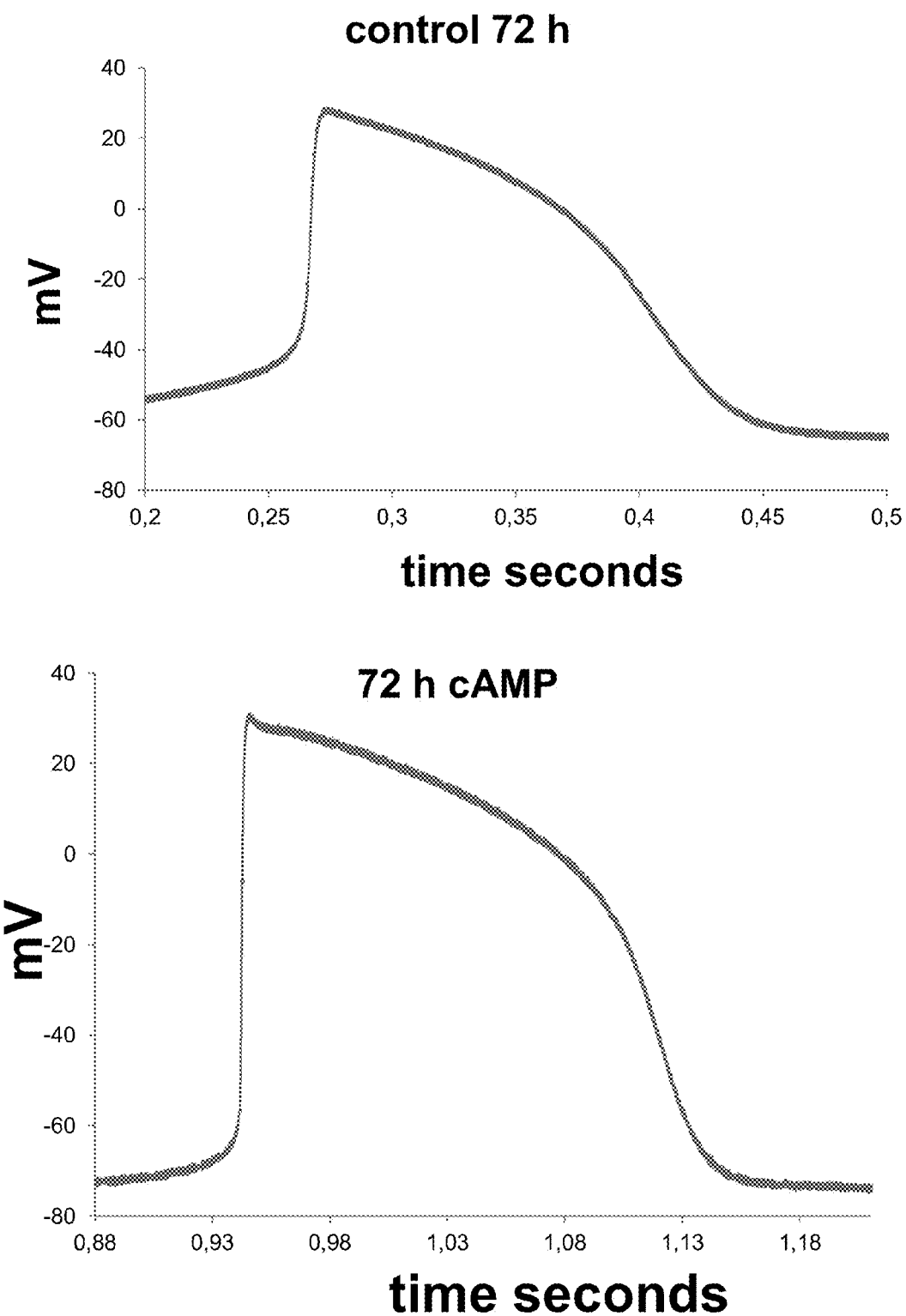

FIG. 6 is a further example of representative action potentials of induced pluripotent stem cells that were treated with or without a cAMP-raising compound dbcAMP for 72 hrs. Whereas the non-treated cells showed relative fetal cardiomyocyte like values, treatment with the cAMP-raising compound leads to action potentials that are more adult cardiomyocyte like. Comparable data may be obtained with human embryonic stem-cell derived cardiomyocytes, other human induced pluripotent stem-cell derived cardiomyocytes and/or with other cAMP-raising compounds.

The invention claimed is:

1. A method of improving maturity of stem-cell derived cardiomyocytes having an embryonic, fetal or immature state of development, wherein the method comprises the step of cultivating said stem-cell derived cardiomyocytes in a defined medium that elevates the cAMP levels of said stem-cell derived cardiomyocytes, by contacting said stem-cell derived cardiomyocytes to an effective amount of a thyroid hormone or thyroid hormone analog and a cAMP-raising compound in said defined medium, thereby improving the maturity of said stem-cell derived cardiomyocytes that show adult-like electrophysiological characteristics after said contacting compared to stem-cell derived cardiomyocytes that have not been contacted with said defined medium comprising the thyroid hormone or thyroid hormone analog, and the cAMP-raising compound.

2. The method of claim 1, wherein the stem-cell derived cardiomyocytes are cultivated in said defined medium comprising the thyroid hormone or thyroid hormone analog, and the cAMP-raising compound for a period selected from the group consisting of at least 2 hours, at least 6 hours, at least 8 hours, at least 12 hours, at least 16 hours, at least 24 hours, at least 30 hours, at least 48 hours, at least 60 hours, and at least 72 hours.

3. The method of claim 1, wherein the improvement in maturity is determined by at least measuring the upstroke velocity of the stem-cell derived cardiomyocytes cultivated in the defined medium comprising the thyroid hormone or thyroid hormone analog, and the cAMP-raising compound, and wherein the upstroke velocity of the stem-cell derived cardiomyocytes cultivated in said medium is higher than the upstroke velocity of stem-cell derived cardiomyocytes not cultivated in said medium.

4. The method of claim 3, wherein the upstroke velocity of the stem-cell derived cardiomyocytes cultivated in said defined medium comprising the thyroid hormone or thyroid hormone analog, and the cAMP-raising compound, is selected from the group consisting of at least 50 V/s, at least 60 V/s, at least 80 V/s, at least 100 V/s, at least 140 V/s, and at least 180 V/s.

5. The method of claim 3, wherein the upstroke velocity of the stem-cell derived cardiomyocytes cultivated in said defined medium comprising the thyroid hormone or thyroid hormone analog, and the cAMP-raising compound, is selected from the group consisting of at least 50 V/s, at least 60 V/s, at least 80 V/s, at least 100 V/s, at least 140 V/s, and at least 180 V/s, and wherein the resting membrane potential of the stem-cell derived cardiomyocytes cultivated in said defined medium is determined and is selected from the group consisting of −66 mV or less, −70 mV or less, −75 mV or less, −78 mV or less, −80 mV or less, −81 mV and −82 mV.

6. The method of claim 1, wherein the improvement in maturity is determined by at least measuring a resting membrane potential of the stem-cell derived cardiomyocytes cultivated in said defined medium comprising the thyroid hormone or thyroid hormone analog, and the cAMP-raising compound, and wherein the resting membrane potential of the stem-cell derived cardiomyocytes cultivated in said defined medium is lower than the resting membrane potential of stem-cell derived cardiomyocytes not cultivated in said defined medium.

7. The method of claim 6, wherein the resting membrane potential of the stem-cell derived cardiomyocytes cultivated in said defined medium comprising the thyroid hormone or thyroid hormone analog, and the cAMP-raising compound, is selected from the group consisting of −66 mV or less, −70 mV or less, −75 mV or less, −78 mV or less, −80 mV or less, −81 mV and −82 mV.

8. The method of claim 1, wherein the cAMP-raising compound is selected from the group consisting of a cAMP-degrading enzyme inhibitor, a cAMP-phosphodiesterase inhibitor, a cAMP-raising drug, a cAMP-raising hormone, an adenylyl cyclase activator, a cAMP analog, IBMX, GLP-1, GIP, glucagon, forskolin, dibutyryl-cAMP, isoproterenol, and combinations thereof.

9. The method according to claim 1, wherein the stem-cell derived cardiomyocytes are stem-cell derived cardiomyocytes obtained by in vitro culturing of stem cells.

10. The method according to claim 1, wherein the stem-cell derived cardiomyocytes are human stem-cell derived cardiomyocytes.

11. The method according to claim 1, wherein the defined medium further comprises:
    (a) 0-5000 mg/L glucose; and
    (b) at least one compound selected from the group consisting of L-carnitine, creatine, taurine, insulin, transferrin, selenium, cholesterol, polyvinylalcohol, α-monothioglycerol, bovine serum albumin, and fatty-acids.

12. The method of claim 11 wherein the defined medium does not comprise glucose.

13. The method of claim 1, wherein the defined medium is a serum-free medium.

14. The method of claim 1, wherein the thyroid hormone or thyroid hormone analog is selected from the group consisting of triiodothyronine and 3,5-diiodothyropropionic acid (DITPA).

* * * * *